(12) United States Patent
Hori et al.

(10) Patent No.: US 10,757,799 B2
(45) Date of Patent: Aug. 25, 2020

(54) PARTICLE BEAM ACCELERATOR AND PARTICLE BEAM THERAPY APPARATUS

(71) Applicant: HITACHI, LTD., Tokyo (JP)

(72) Inventors: Chishin Hori, Tokyo (JP); Takamichi Aoki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/604,316

(22) PCT Filed: Mar. 6, 2018

(86) PCT No.: PCT/JP2018/008487
§ 371 (c)(1),
(2) Date: Oct. 10, 2019

(87) PCT Pub. No.: WO2018/193733
PCT Pub. Date: Oct. 25, 2018

(65) Prior Publication Data
US 2020/0128659 A1 Apr. 23, 2020

(30) Foreign Application Priority Data
Apr. 18, 2017 (JP) .................. 2017-081790

(51) Int. Cl.
*H05H 13/00* (2006.01)
*H05H 7/04* (2006.01)
(Continued)

(52) U.S. Cl.
CPC .............. *H05H 7/04* (2013.01); *A61N 5/1077* (2013.01); *G21K 5/04* (2013.01); *H05H 13/005* (2013.01);
(Continued)

(58) Field of Classification Search
CPC .......... H01J 25/00; H01J 25/50; H05H 13/00; H05H 13/005; H05H 13/02; H05H 13/04; A61N 5/00; A61N 5/1077
See application file for complete search history.

(56) References Cited

U.S. PATENT DOCUMENTS

| | | | |
|---|---|---|---|
| 8,344,340 B2 * | 1/2013 | Gall | A61N 5/10 250/505.1 |
| 9,155,186 B2 * | 10/2015 | Zwart | H05H 7/04 |

(Continued)

FOREIGN PATENT DOCUMENTS

| | | |
|---|---|---|
| JP | 2013-534700 A | 9/2013 |
| WO | 2016/092621 A1 | 6/2016 |

OTHER PUBLICATIONS

International Search Report of PCT/JP2018/008487 dated Apr. 24, 2018.

*Primary Examiner* — Jason Crawford
(74) *Attorney, Agent, or Firm* — Mattingly & Malur, PC

(57) ABSTRACT

A magnet device that includes upper and lower disk-shaped return yokes, a pair of upper magnetic pole and lower magnetic pole respectively fixed to a disk-shaped surface of the upper return yoke and a disk-shaped surface of the lower return yoke, in which a space to circulate and accelerate an ion beam is formed between the upper magnetic pole and the lower magnetic pole. The upper magnetic pole and the lower magnetic pole have a plurality of concave and convex parts along a track along which the ion beam circulates, are plane-symmetrical with respect to a horizontal symmetry plane formed by the track along which an ion beam circulates, and are plane-symmetrical to one of the vertical planes vertical to the horizontal symmetry plane. Also, the magnetic pole intervals between the concave parts of the upper magnetic pole and the lower magnetic pole are different from each other.

7 Claims, 12 Drawing Sheets

(51) Int. Cl.
*G21K 5/04* (2006.01)
*A61N 5/10* (2006.01)

(52) U.S. Cl.
CPC ............... *A61N 2005/1087* (2013.01); *H05H 2007/046* (2013.01)

(56) References Cited

U.S. PATENT DOCUMENTS

| | | | |
|---|---|---|---|
| 9,185,789 B2* | 11/2015 | Zwart | H05H 13/02 |
| 10,306,745 B2* | 5/2019 | Aoki | A61N 5/10 |
| 10,548,212 B2* | 1/2020 | Aoki | H05H 13/04 |
| 2009/0314960 A1* | 12/2009 | Balakin | A61N 5/1049 250/492.3 |
| 2011/0118529 A1* | 5/2011 | Balakin | A61N 5/10 600/1 |
| 2013/0141019 A1 | 6/2013 | Kleeven | |
| 2014/0371511 A1* | 12/2014 | Zwart | H05H 13/02 600/1 |
| 2017/0128746 A1* | 5/2017 | Zwart | A61N 5/1044 |
| 2017/0199506 A1* | 7/2017 | Jones | G05B 19/19 |
| 2017/0303384 A1* | 10/2017 | Aoki | H05H 7/08 |
| 2017/0339778 A1* | 11/2017 | Aoki | A61N 5/1077 |
| 2019/0126074 A1* | 5/2019 | Ebina | A61N 5/1081 |
| 2019/0232085 A1* | 8/2019 | Hori | A61N 5/1001 |

* cited by examiner

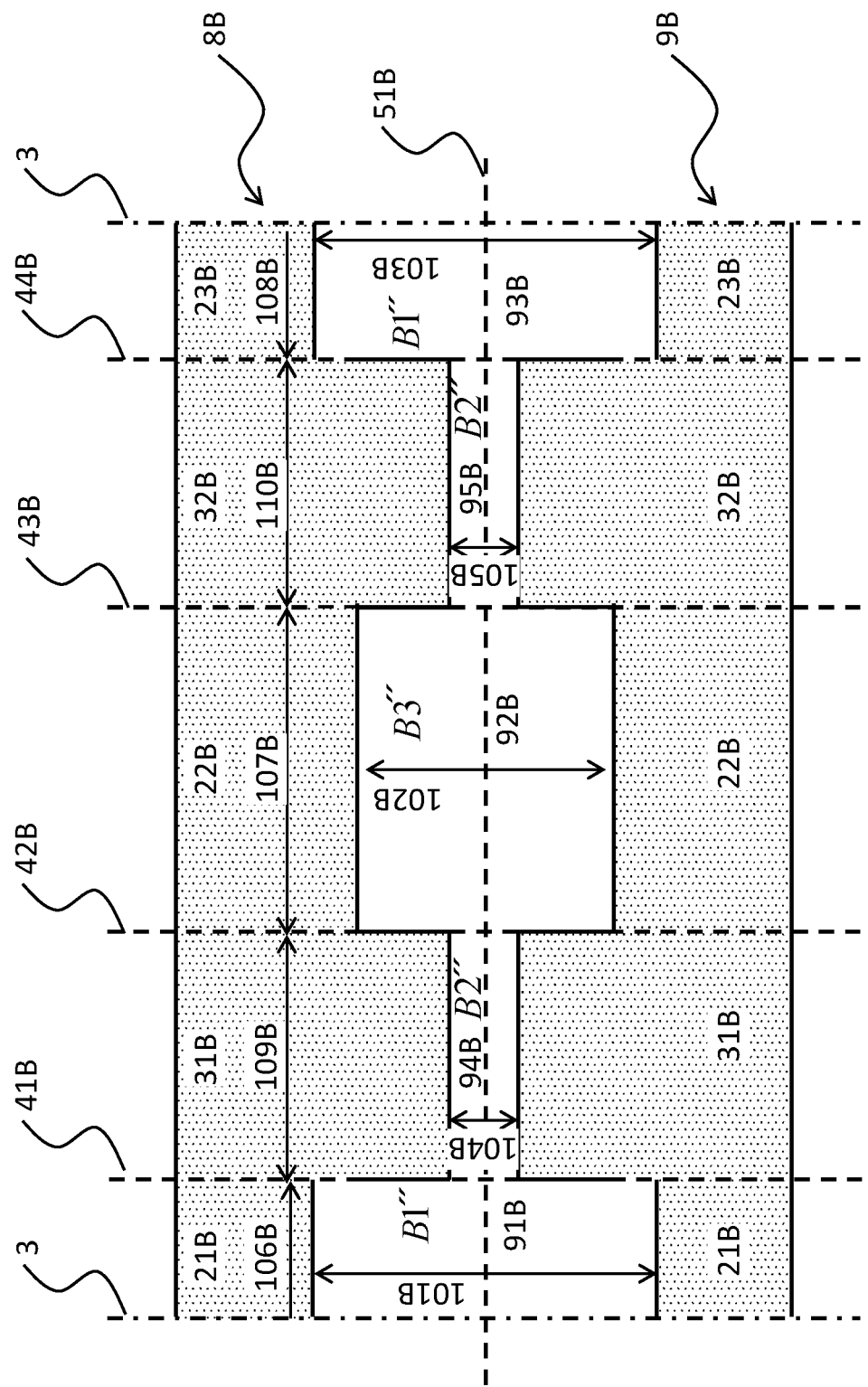

PARTICLE BEAM ACCELERATOR AND PARTICLE BEAM THERAPY APPARATUS

TECHNICAL FIELD

The present invention relates to a particle beam accelerator and a particle beam therapy apparatus.

BACKGROUND ART

As a background technique of the invention, there is a technique described in PTL 1. PTL 1 describes an accelerator, as an accelerator capable of efficiently emitting ion beams having different energies, including a return yoke and a vacuum container, in which an incidence electrode is disposed closer to an incidence side of a beam emitting path in the return yoke than a central axis of the vacuum container, magnetic poles are radially disposed from the incidence electrode around the incidence electrode in the return yoke, and concave parts are alternately disposed with the magnetic poles in a circumferential direction of the return yoke; and in the vacuum container, a track concentric region is formed in which a plurality of beam circulating tracks are centered on the incidence electrode, and around the track concentric region, a track eccentric region is formed in which a plurality of beam circulating tracks are decentered from the incidence electrode, the beam circulating tracks are dense between the incidence electrode and an incidence of the beam emitting path in the track eccentric region, and an interval between the beam circulating tracks is wider on a 180° opposite side of the incidence of the beam emitting path with the incidence electrode as a base point.

PRIOR ART LITERATURE

Patent Literature

PTL 1: WO2016/092621

SUMMARY OF INVENTION

Technical Problem

There has been proposed a cyclotron accelerator for efficiently emitting beams with different energies. An example of such a cyclotron accelerator includes the accelerator described in PTL 1.

In the accelerator of PTL 1, a positional relationship of the beam tracks having different energies is not substantially concentric, and the beams move in one direction along a straight line with a beam track center from low energy to high energy. Therefore, an aggregation region where an interval (turn separation) between adjacent beam tracks is narrow and a discrete region where the interval is wide on the contrary are at different positions in a beam circulating direction. That is, since there is a region where the turn separation of a high energy beam is larger than that of a substantially concentric beam track, it is easy to apply a magnetic field and an electric field for extracting a beam having a desired energy to the beam having a desired energy, and it is easy to selectively extract the beam.

The above PTL 1 discloses a magnetic field distribution (FIG. 10) for realizing a beam track having the aggregate region and the discrete region, and a magnetic pole shape (FIG. 30) for realizing the magnetic field distribution. The extraction efficiency of the beam extraction according to the technique of PTL 1 is improved compared with a method in which a scattered body is required for the beam extraction.

As described above, in order to further improve the extraction efficiency of the beam, a narrowing of the beam aggregation region and an enlargement of the discrete region are effective.

Accordingly, it is an object of the invention to provide a particle beam accelerator and a particle beam therapy apparatus which have beam extraction efficiency higher than that in the related art.

Solution to Problem

The invention includes a plurality of means for solving the above problems, and one example thereof relates to a particle beam accelerator, including: a magnet device that includes return yokes, and a pair of magnetic poles fixed to flat surfaces of the return yokes, in which a space to circulate and accelerate an ion beam is formed between the pair of magnetic poles, and the pair of magnetic poles have a plurality of concave structures and convex structures along a track along which the ion beam circulates, are plane-symmetrical with respect to a track plane formed by the track along which the ion beam circulates, and are plane-symmetrical to one of vertical planes vertical to the track plane, and distances between the plurality of concave structure parts of the pair of magnetic poles are different.

Advantageous Effect

According to the invention, it is possible to provide a particle beam accelerator and a particle beam therapy apparatus which have beam extraction efficiency higher than that in the related art.

BRIEF DESCRIPTION OF DRAWINGS

FIG. 12 is a cross-sectional view along a beam track of a magnetic pole of the magnet device illustrated in FIG. 11.

DESCRIPTION OF EMBODIMENTS

Embodiments of a particle beam accelerator and a particle beam therapy apparatus of the invention will be described below with reference to the drawings.

First Embodiment

A particle beam accelerator and a particle beam therapy apparatus according to a first embodiment of the invention will be described with reference to FIG. 1 to FIG. 10. First, a configuration of the particle beam therapy system will be described with reference to FIG. 1.

Figure 1:
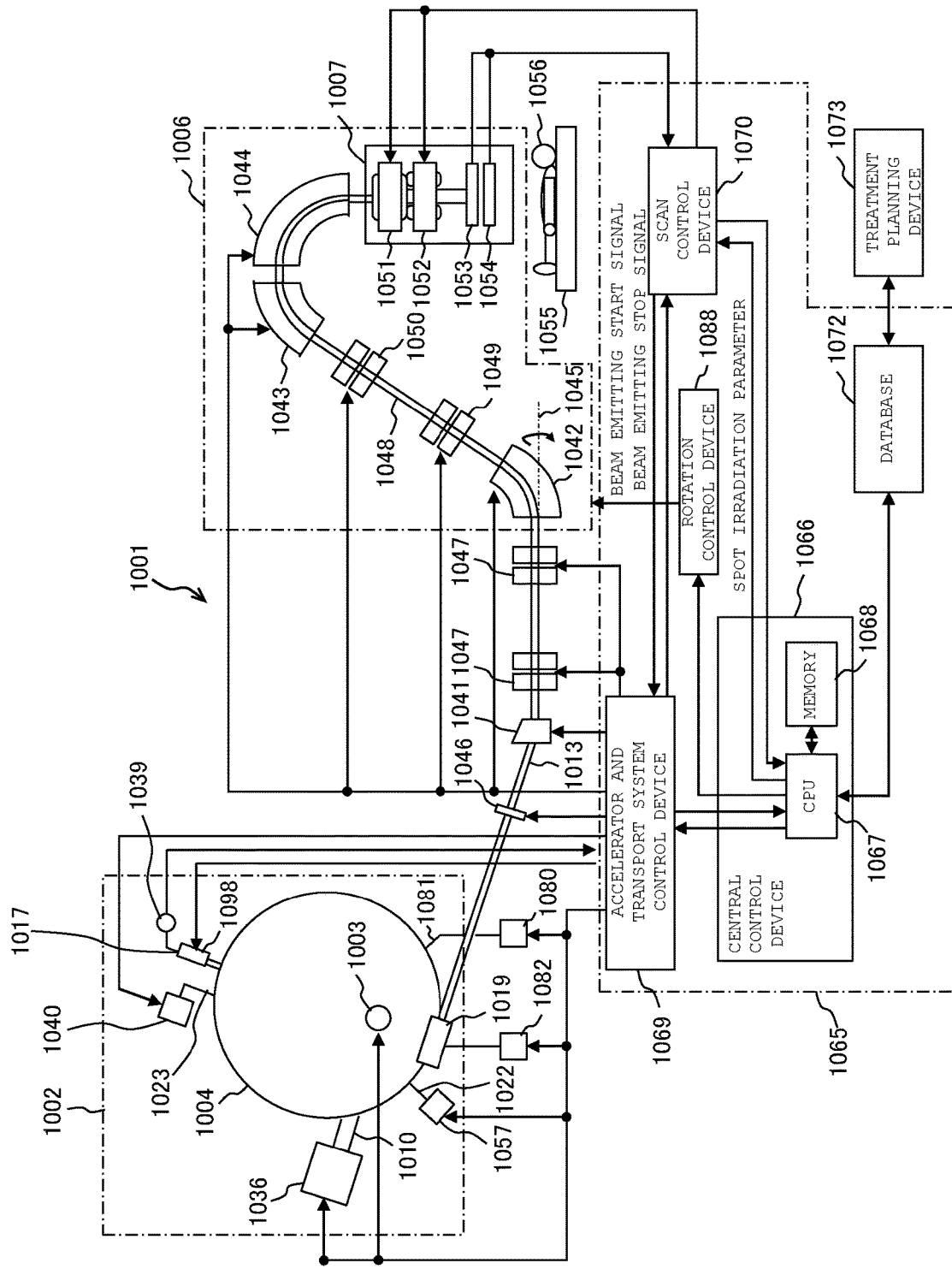
FIG. 1 is configuration view of a particle beam therapy apparatus according to a first embodiment.

In FIG. 1, a particle beam therapy apparatus 1001 is disposed in a building (not shown) and provided on a floor surface of the building. The particle beam therapy apparatus 1001 includes an ion beam generation device 1002, a beam transport system 1013, a rotating gantry 1006, an irradiation device 1007, and a control system 1065. The ion beam generation device 1002 includes an ion source 1003 and an accelerator (particle beam accelerator) 1004 to which the ion source 1003 is connected.

The beam transport system 1013 includes a beam path 1048 that reaches the irradiation device 1007. In the beam path 1048, a plurality of quadruple electromagnets 1046, a deflection electromagnet 1041, a plurality of quadruple electromagnets 1047, a deflection electromagnet 1042, quadruple electromagnets 1049, 1050, and deflection electromagnets 1043, 1044 are disposed in this order from the accelerator 1004 to the irradiation device 1007. A part of the beam path 1048 of the beam transport system 1013 is provided in the rotating gantry 1006, and the deflection electromagnet 1042, the quadruple electromagnets 1049, 1050, and the deflection electromagnets 1043, 1044 are also provided in the rotating gantry 1006. The beam path 1048 is connected to an emission channel 1019 provided in the accelerator 1004.

The rotating gantry 1006 is a rotating device that rotates around a rotation axis 1045 and swivels the irradiation device 1007 around the rotation axis 1045.

The irradiation device 1007 includes two scanning electromagnets (ion beam scanning devices) 1051, 1052, a beam position monitor 1053, and a dose monitor 1054. The scanning electromagnets 1051, 1052, the beam position monitor 1053, and the dose monitor 1054 are disposed along a central axis of the irradiation device 1007, that is, along a beam axis. The scanning electromagnets 1051, 1052, the beam position monitor 1053, and the dose monitor 1054 are disposed in a casing (not shown) of the irradiation device 1007, and the beam position monitor 1053 and the dose monitor 1054 are disposed on a downstream of the scanning electromagnets 1051, 1052. The scanning electromagnet 1051 deflects an ion beam in a plane vertical to the central axis of the irradiation device 1007 to operate in a y direction, and the scanning electromagnet 1052 deflects the ion beam in the plane and performs scanning in an x direction orthogonal to the y direction.

The irradiation device 1007 is attached to the rotating gantry 1006 and is disposed on a downstream of the deflection electromagnet 1044. A treatment table 1055 on which a patient 1056 lies is disposed so as to face the irradiation device 1007.

The control system 1065 includes a central control device 1066, an accelerator and transport system control device 1069, a scan control device 1070, a rotation control device 1088, and a database 1072. The central control device 1066 includes a central processing unit (CPU) 1067 and a memory 1068 that is connected to the CPU 1067. The accelerator and transport system control device 1069, the scan control device 1070, the rotation control device 1088, and the database 1072 are connected to the CPU 1067. The particle beam therapy apparatus 1001 includes a treatment planning device 1073, and the treatment planning device 1073 is connected to the database 1072.

A beam current measurement device 1098 includes a mobile device 1017 and a position detector 1039.

A high frequency power supply 1036 applies a voltage to a high frequency acceleration electrode (not shown) provided in the accelerator 1004 through a waveguide 1010 to accelerate the ion beam.

Figure 2:
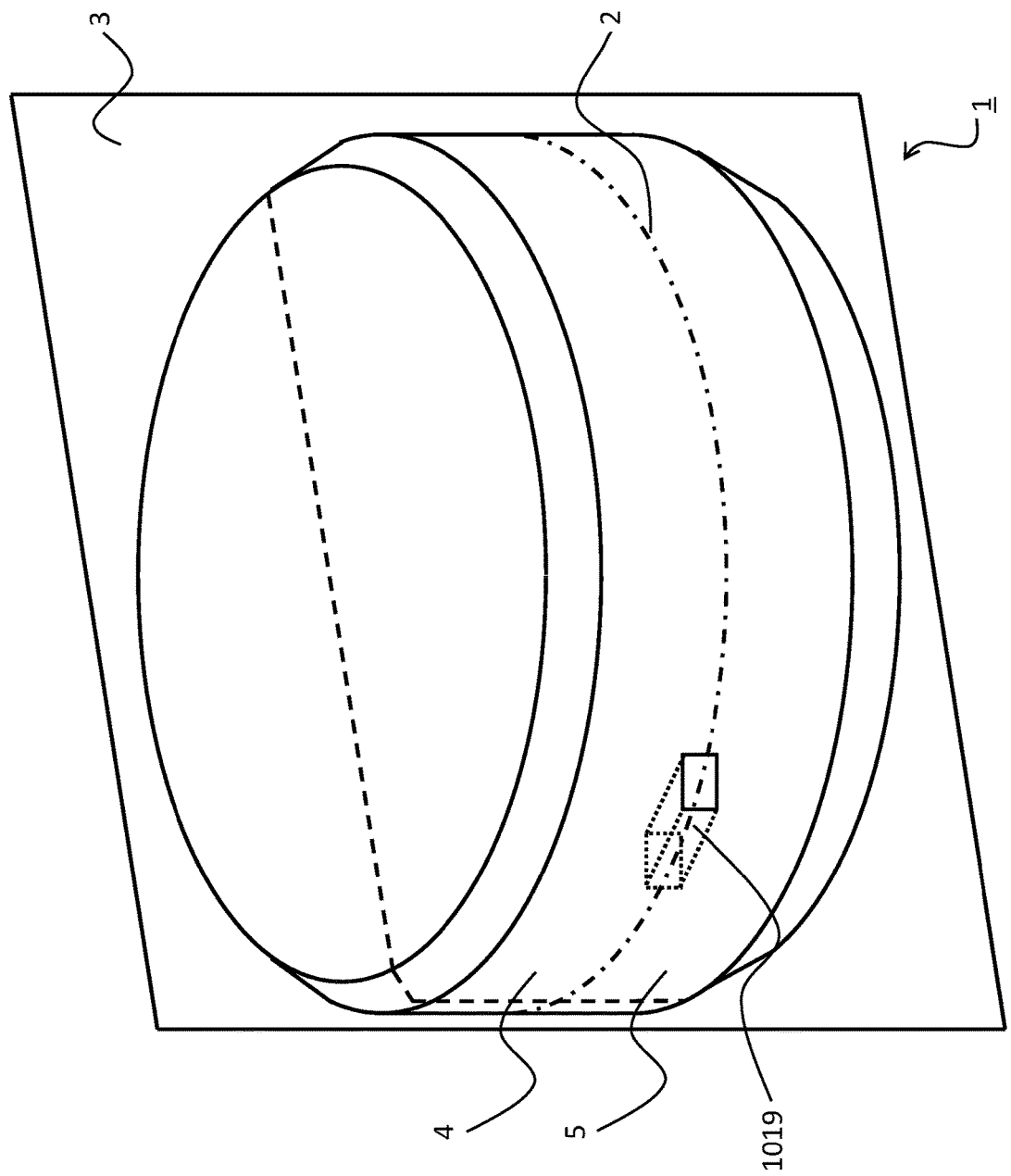
FIG. 2 is a perspective view of a magnet device disposed in an accelerator of the particle beam therapy apparatus according to the first embodiment.

Next, the structure of a magnet device 1 used in the accelerator 1004 will be described with reference to FIG. 2 to FIG. 5. FIG. 2 is a perspective view of the magnet device 1.

As illustrated in FIG. 2, an outer shell of the accelerator 1004 is formed by the magnet device 1.

The magnet device 1 mainly includes an upper return yoke 4 and a lower return yoke 5 that have a substantially disk-like shape when viewed from a vertical direction, and the upper return yoke 4 and the lower return yoke 5 have substantially vertical symmetrical shapes with respect to a horizontal symmetry plane (track plane) 2. The horizontal symmetry plane 2 is a plane generally passing through the center of the magnet device 1 in the vertical direction and parallel to a track drawn by the ions during acceleration. In addition, the upper return yoke 4 and the lower return yoke 5 have symmetrical shapes with respect to a vertical symmetry plane 3 that is vertical to the horizontal symmetry plane 2 and is generally a plane passing through a center with respect to the horizontal symmetry plane 2 of the magnet device 1. In FIG. 2, an intersecting part of the horizontal symmetry plane 2 with respect to the magnet device 1 is indicated by a dashed line and an intersecting part of the vertical symmetry plane 3 with respect to the magnet device 1 is indicated by a broken line.

Figure 3:
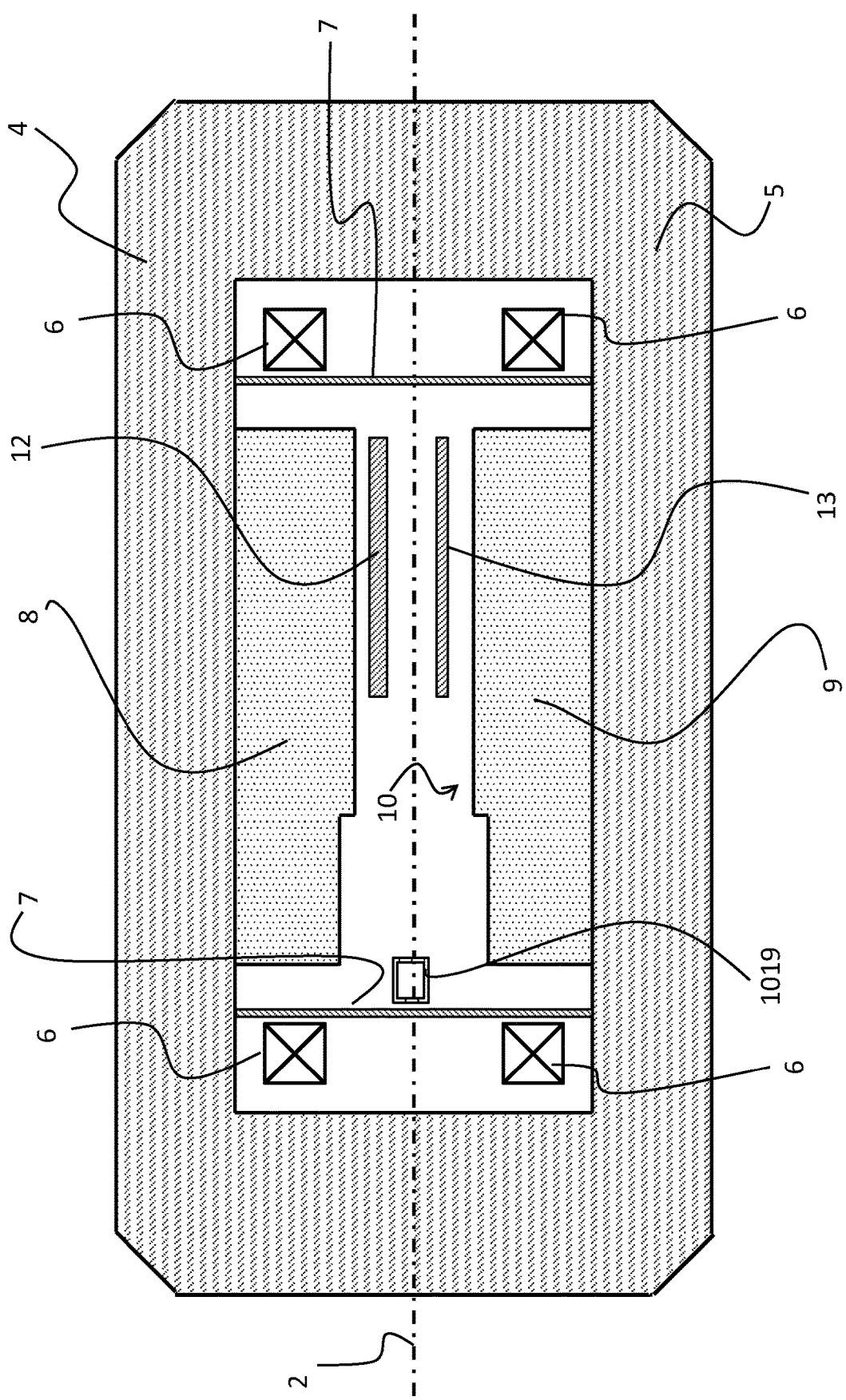
FIG. 3 is a cross-sectional view of the magnet device disposed in the accelerator of the particle beam therapy apparatus according to the first embodiment.

FIG. 3 is a cross-sectional view of the magnet device 1 along the vertical symmetry plane 3. As illustrated in FIG. 3, in a space surrounded by the upper return yoke 4 and the lower return yoke 5, coils 6 are disposed plane-symmetrically with respect to the horizontal symmetry plane 2.

The coils 6 are connected to a coil excitation power supply 1057 via a coil lead wiring 1022 illustrated in FIG. 1. A vacuum container 7 is provided on an inner side of the coils 6 in the space surrounded by the upper return yoke 4 and the lower return yoke 5.

Inside the vacuum container 7, an upper magnetic pole 8 disposed on a surface of the upper return yoke 4 facing the lower return yoke 5, and a lower magnetic pole 9 disposed on a surface of the lower return yoke 5 facing the upper return yoke 4 are disposed to be plane-symmetrical with respect to the horizontal symmetry plane 2, the upper magnetic pole 8 is coupled to the upper return yoke 4, and the lower magnetic pole 9 is coupled to the lower return yoke 5. A space for circulating and accelerating the ion beam is formed between the upper magnetic pole 8 and the lower magnetic pole 9.

In addition, extraction electromagnets 12, 13 are disposed to be plane-symmetrical with respect to the horizontal symmetry plane 2. The extraction electromagnets 12, 13 are connected to an extraction electromagnet power supply 1040 via an extraction electromagnet extraction wiring 1023 illustrated in FIG. 1. By applying a current so as to apply a magnetic field to the extraction electromagnets 12, 13, the beam track changes from an equilibrium track, and the beam reaches the emission channel 1019 illustrated in FIG. 1. The emission channel 1019 is provided with an electromagnet (not shown) and is connected to an emission channel power supply 1082 illustrated in FIG. 1. By applying a current from the emission channel power supply 1082 to the electromagnet provided in the emission channel 1019, the ion beam that has reached the emission channel 1019 is adjusted and sent to the beam transport system 1013.

Figure 4:
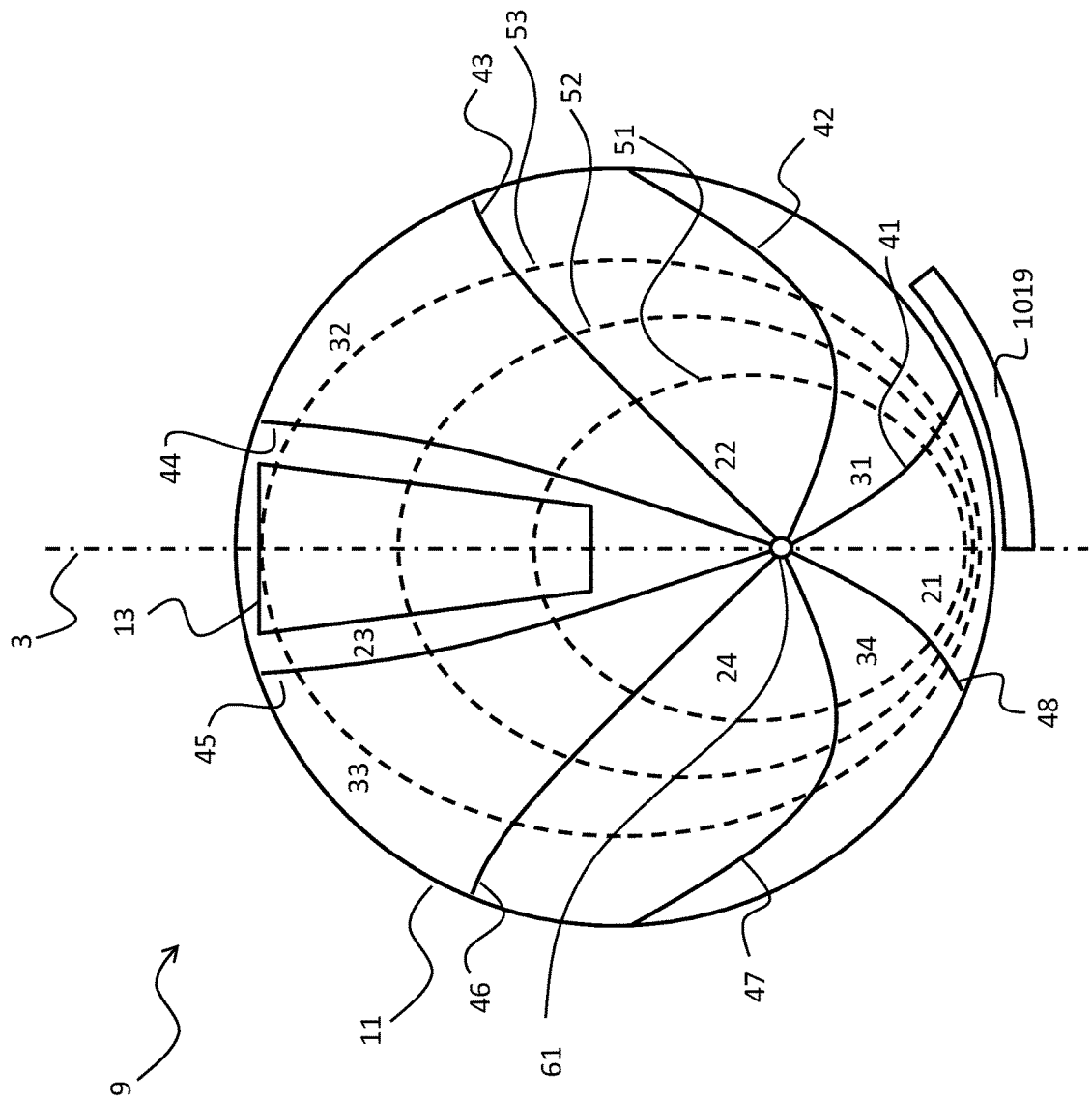
FIG. 4 is a plan view of a magnetic pole surface of the magnet device disposed in the accelerator of the particle beam therapy apparatus according to the first embodiment.
Figure 5:
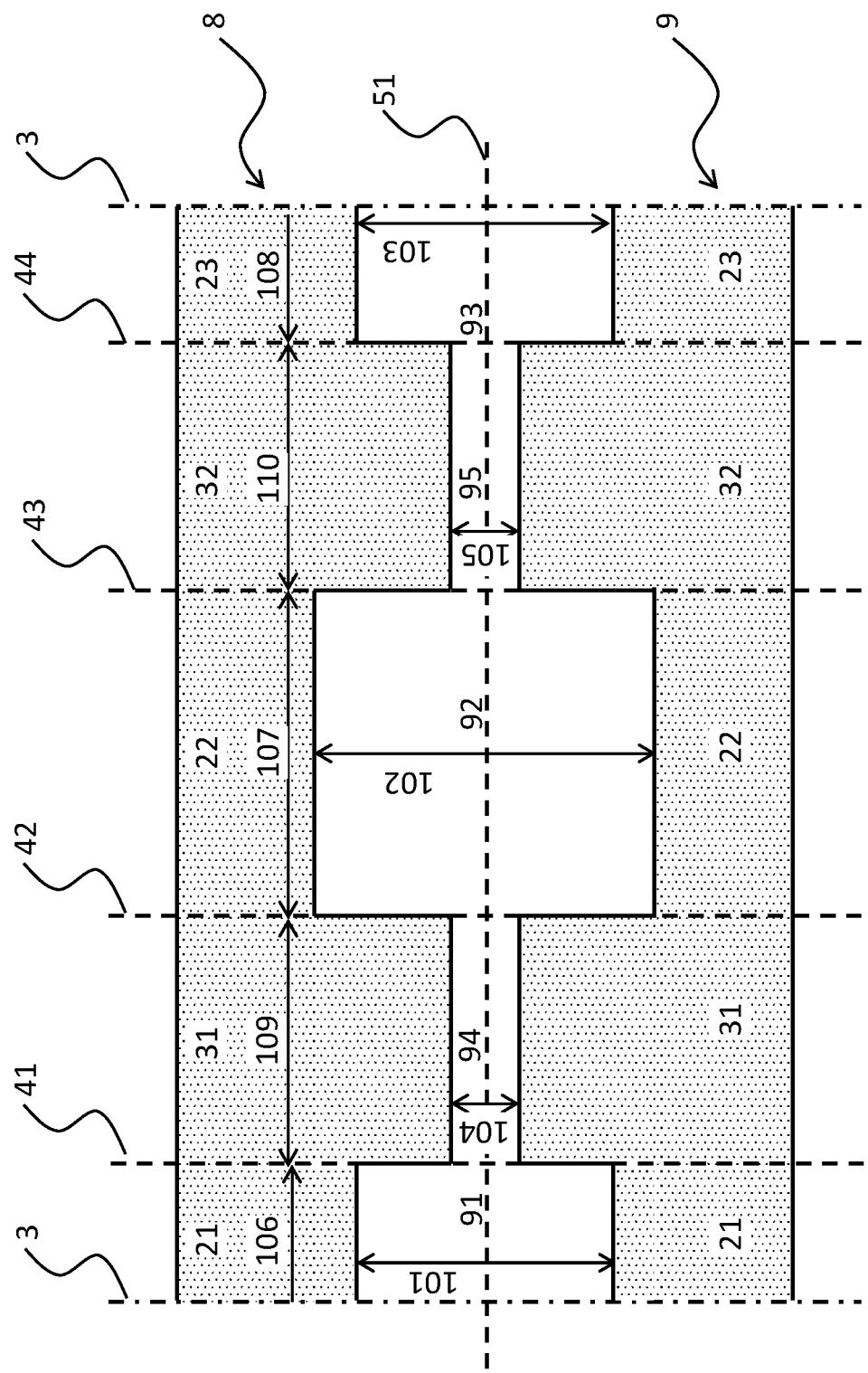
FIG. 5 is a cross-sectional view along a beam track of a magnetic pole of the magnet device illustrated in FIG. 4.

Since the magnet device 1 has a structure vertical symmetrical with respect to the horizontal symmetry plane 2, hereinafter, a magnetic pole surface 10 of the lower magnetic pole 9 will be described in detail with reference to FIG. 4 and FIG. 5. FIG. 4 is a plan view of the magnetic pole surface 10 viewed from the horizontal symmetry plane 2. FIG. 5 is a cross-sectional view of the upper magnetic pole 8 and the lower magnetic pole 9 along a beam track 51 illustrated in FIG. 4.

On the magnetic pole surface 10 of the lower magnetic pole 9, as illustrated in FIG. 4, concave parts 21, 22, 23 and 24 and convex parts 31, 32, 33 and 34 that are indicated by solid lines in a circulating direction of circulating beam tracks 51, 52 and 53 of the ion beam are alternately arranged, and are plane-symmetrical with respect to the vertical symmetry plane 3. An extraction electromagnet 13 is disposed directly above the concave part 23. As is clear from the figure, in the structure of the magnet device 1 of the present embodiment, the upper magnetic pole 8 and the lower magnetic pole 9 have a plurality of concave structures and convex structures along the track along which the ion beam circulates, and are plane-symmetrical with respect to the track plane formed by the beam tracks, and only one vertical symmetry plane 3 is specified as a plane vertical to the track planes that are plane-symmetrical.

Each of the concave parts 21, 22, 23, and 24, and convex parts 31, 32, 33, and 34 has substantially a fan shape, and there is a space 61 for disposing an ion incident device at a position where apexes of the fan shapes of the concave parts 21, 22, 23, and 24, and convex parts 31, 32, 33, and 34 are aggregated. The space 61 may be considered to be an ion incident position on the magnetic pole surface 10. An incidence electrode (not shown) is provided in the space 61, and as illustrated in FIG. 1, the incidence electrode is connected to an incidence electrode power supply 1080 via an incidence electrode lead wiring 1081.

As illustrated in FIG. 4, shapes of the concave parts 21, 22, 23 and 24 are not all the same. Specifically, although the concave part 22 and the concave part 24 have shapes symmetrical with respect to the vertical symmetry plane 3, the concave part 22 and the concave part 24 have shapes different from those of the concave part 21 and the concave part 23. That is, areas of the concave parts 21, 22, 23 and 24 when projected onto the horizontal symmetry plane 2 are not all the same, and the concave part 22 and the concave part 24 have the same area, while the concave part 21 and the concave part 23 have different areas.

As illustrated in FIG. 5, a valley region 91 sandwiched by upper and lower concave parts 21, a hill region 94 sandwiched between upper and lower convex parts 31, a valley region 92 sandwiched between upper and lower concave parts 22, a hill region 95 sandwiched between upper and lower convex parts 32, and a valley region 93 sandwiched between upper and lower concave parts 23 are arranged along the beam track 51. Boundary surfaces 41, 42, 43 and 44 are substantially vertical to the horizontal symmetry plane 2. Similarly, boundary surfaces 45, 46, 47 and 48 are also generally vertical to the horizontal symmetry plane 2.

Design values of a magnetic pole interval 101 between the upper magnetic pole 8 and the lower magnetic pole 9 in the valley region 91, a magnetic pole interval 102 between the upper magnetic pole 8 and the lower magnetic pole 9 in the valley region 92, and a magnetic pole interval 103 between the upper magnetic pole 8 and the lower magnetic pole 9 in the valley region 93 are not the same value, but different values. The magnetic pole interval 102 is larger than the magnetic pole interval 101 and the magnetic pole interval 103. Therefore, a magnetic field in the valley region 91 or the valley region 93 is stronger than a magnetic field in the valley region 92.

Similar to the magnetic pole intervals 101, 102, and 103, design values of a magnetic pole interval 104 between the upper magnetic pole 8 and the lower magnetic pole 9 in the hill region 94 and a magnetic pole interval 105 between the upper magnetic pole 8 and the lower magnetic pole 9 in the hill region 95 are also different.

In addition, in the magnet device 1, a magnetic pole width 106 of the concave part 21, a magnetic pole width 107 of the concave part 22, and a magnetic pole width 108 of the concave part 23 are not a same width, but are different widths. Specifically, the magnetic pole width 107 is wider than the magnetic pole width 106 and the magnetic pole width 108. Further, the magnetic pole width 109 of the convex part 31 and the magnetic pole width 110 of the convex part 32 are also different. The magnetic pole width 107 of the concave part 22 and the magnetic pole width of the concave part 24 have the same value, the magnetic pole width 109 of the convex part 31 and the magnetic pole width of the convex part 34 have the same value, and the magnetic pole width 110 of the convex part 32 and the magnetic pole width of the convex part 33 have the same value.

Figure 6:
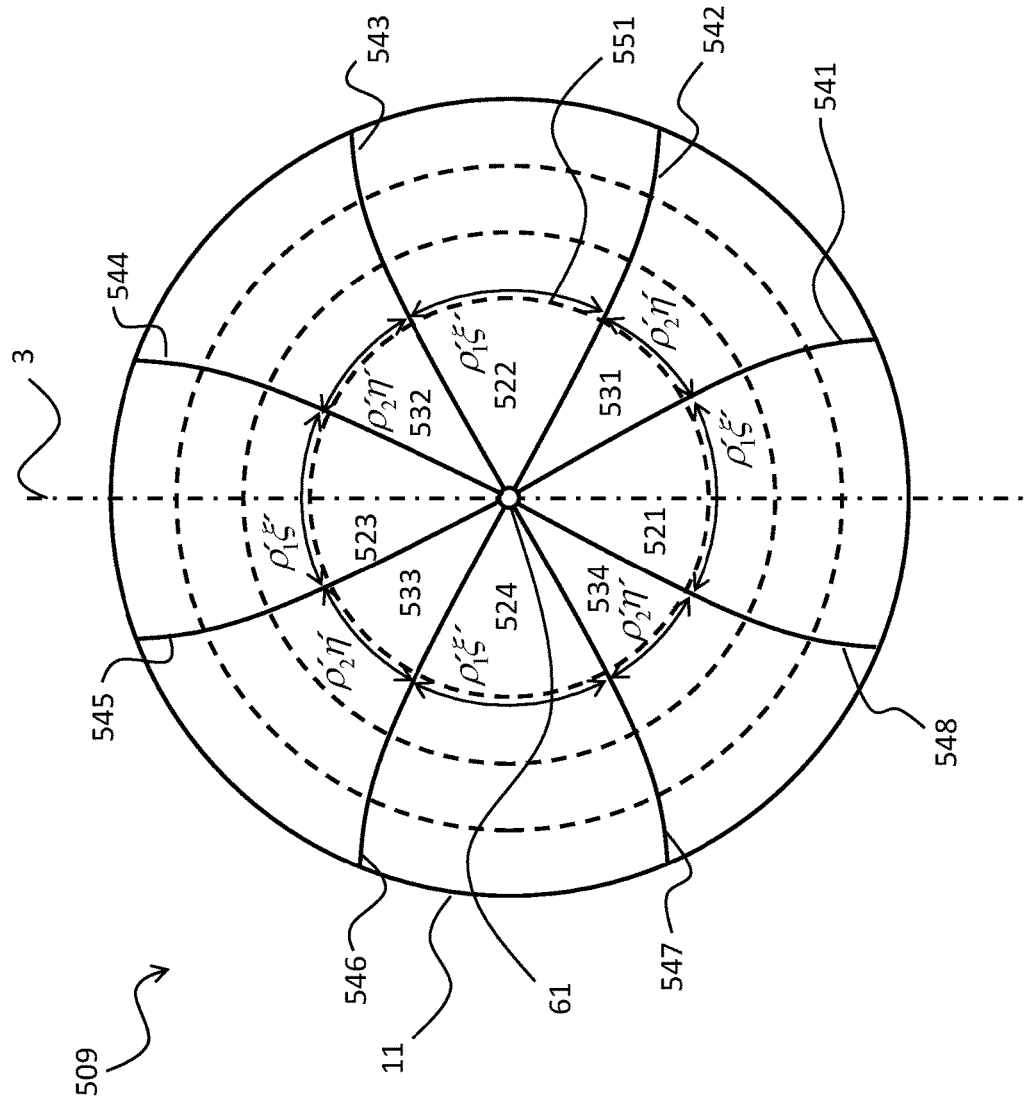
FIG. 6 is a plan view of a magnetic pole surface of a general sector type cyclotron magnet device.
Figure 7:
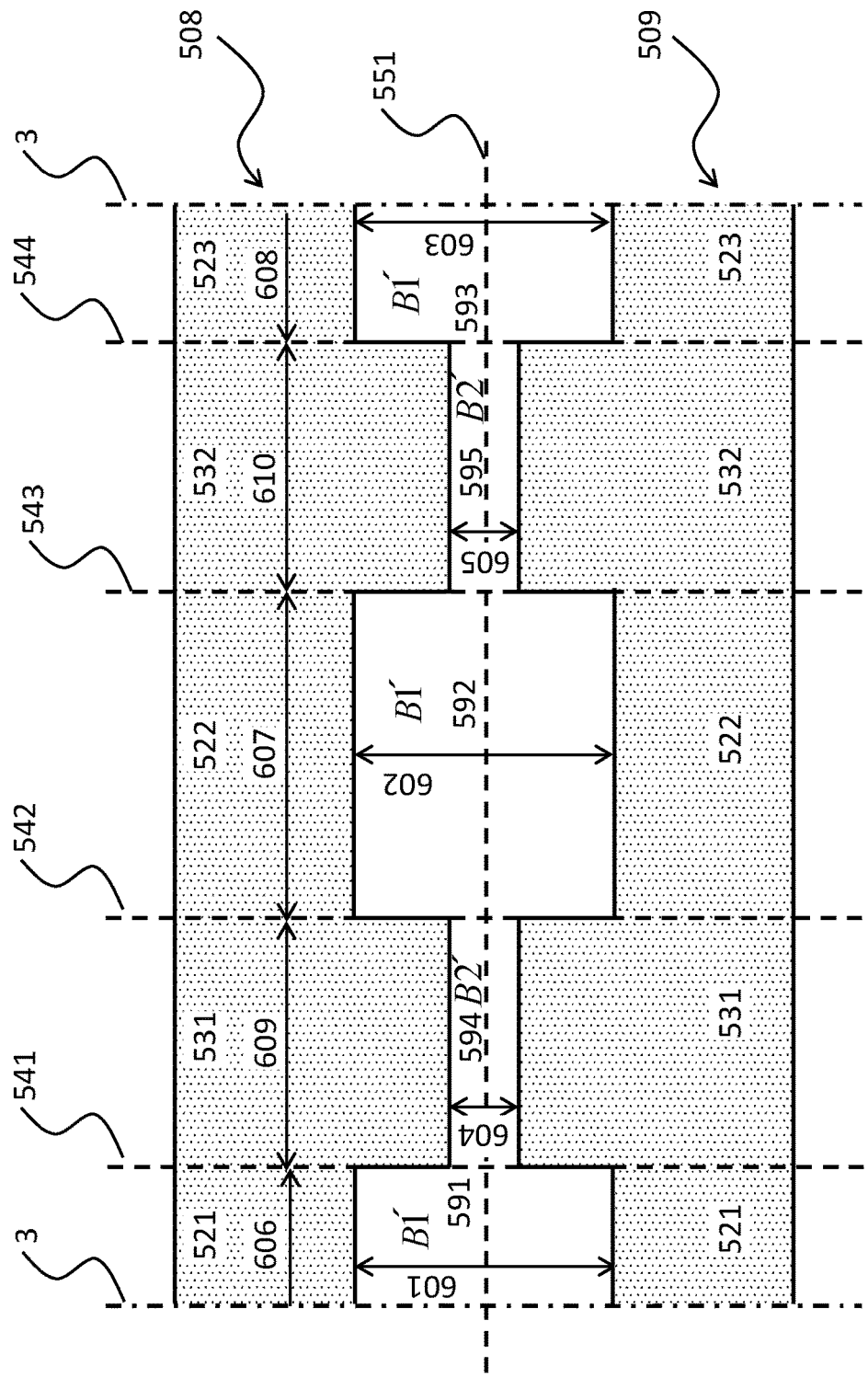
FIG. 7 is a cross-sectional view of a magnetic pole of the general sector type cyclotron magnet device along a beam track.

Next, a magnet device for a general sector type cyclotron will be described with reference to FIG. 6 and FIG. 7 in order to compare and explain an effect of the structure described above. FIG. 6 is a plan view of a lower magnetic pole 509 of a magnet device. FIG. 7 is a cross-sectional view of an upper magnetic pole 508 and the lower magnetic pole 509 along a beam track 551 illustrated in FIG. 6.

As illustrated in FIG. 6, in a general sector type cyclotron, a plurality of concave parts 521, 522, 523, and 524 are designed to have the same shape, and convex parts 531, 532, 533, and 534 are designed to have the same shape.

Here, a beam curvature radius in the concave parts 521, 522, 523, and 524 is set as $\rho_1'$, and a beam deflection angle thereof is set as $\xi'$. In addition, a beam curvature radius in the convex parts 531, 532, 533, and 534 is set as $\rho_2'$, and a beam deflection angle thereof is set as $\eta'$. In addition, magnetic field intensity in the concave parts 521, 522, 523, and 524 is set as B1', magnetic field intensity in the convex parts 531, 532, 533, and 534 is set as B2', and an average magnetic field along the beam track is set as B'. Then, relationships illustrated in following Equations (1) and (2) are established.

$$\xi' + \eta' = \frac{\pi}{2} \qquad \text{(Equation 1)}$$

$$\frac{B2' - B1'}{B1'}\xi' = \frac{\pi}{2}\frac{B2' - B'}{B'} \qquad \text{(Equation 2)}$$

In addition, as illustrated in FIG. 7, magnetic pole intervals 601, 602 and 603 are equal, and the magnetic field intensity in valley regions 591, 592 and 593 is equal to B1'.

In addition, a magnetic pole interval 604 of the hill region 594 and a magnetic pole interval 605 of the hill region 595 are also equal, and the magnetic field intensity is also equal to B2'.

Further, a magnetic pole width 606 of the concave part 521, a magnetic pole width 607 of the concave part 622, and a magnetic pole width 608 of the concave part 623 have the same value ($\rho_1'\xi'$), and a magnetic pole width 609 of the convex part 631 and a magnetic pole width 610 of the convex part 632 have the same value ($\rho_2'\eta'$).

Boundary surfaces 541, 542, 543, 544, 545, 546, 547, and 548 are generally substantially vertical to the horizontal symmetry plane 2.

Figure 8:
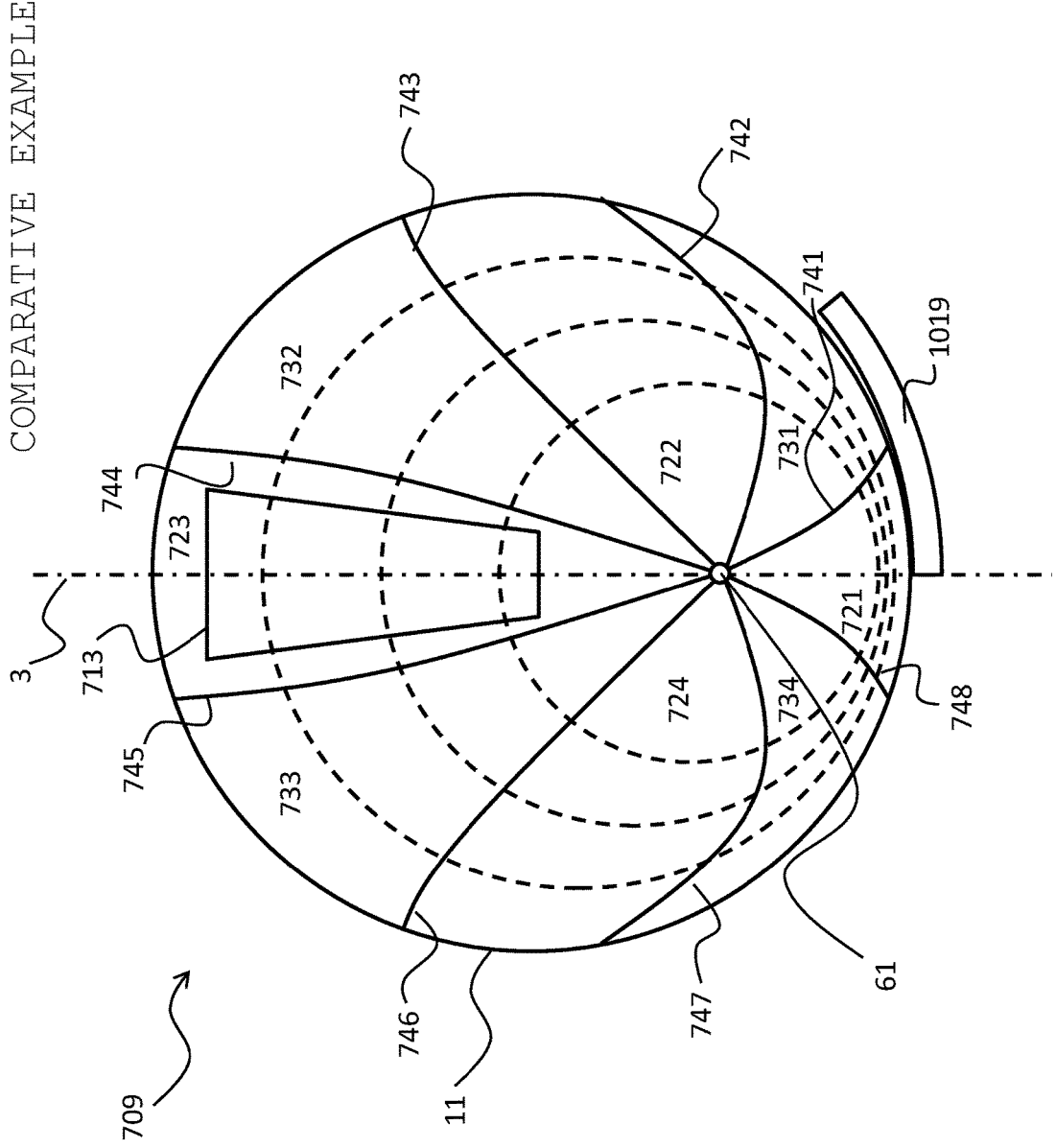
FIG. 8 is a plan view of a magnetic pole surface of a comparative example of an accelerator magnet device in which a beam track in the general sector type cyclotron magnet device is decentered.

The beam track is concentric in the general sector type cyclotron described with reference to FIG. 6 and FIG. 7, but in FIG. 8, a magnet device in which the magnetic pole shape is changed so as to make the beam track eccentric is considered. FIG. 8 is a plan view of a magnetic pole surface of a lower magnetic pole 709 of the magnet device viewed from the horizontal symmetry plane 2. The magnet device that is provided with the lower magnetic pole 709 illustrated in FIG. 8 has the same magnetic field distribution along the beam track of the magnet device illustrated in FIG. 6 and FIG. 7.

As illustrated in FIG. 8, when the beam track is decentered, a beam turn separation in a valley region sandwiched by upper and lower concave parts 723 in FIG. 8 is larger than a beam turn separation of in the valley region 523 of FIG. 6. Therefore, a current is flowed to an extraction electromagnet 713 so as to apply a magnetic field, so that the beam having a target energy can be extracted.

In FIG. 8, magnetic pole intervals in a valley region sandwiched by upper and lower concave parts 721, a valley region sandwiched by upper and lower concave parts 722, the valley region sandwiched by the upper and lower concave parts 723, and a valley region sandwiched by upper and lower concave parts 724 have the same value. In addition, magnetic pole intervals in a hill region sandwiched between upper and lower convex parts 731 and a hill region sandwiched between upper and lower convex parts 734 have the same value, and magnetic pole intervals in a hill region sandwiched between upper and lower convex parts 732 and a hill region sandwiched between upper and lower convex parts 733 have the same value.

Boundary surfaces 741, 742, 743, 744, 745, 746, 747 and 748 are substantially vertical to the horizontal symmetry plane 2.

Figure 9:
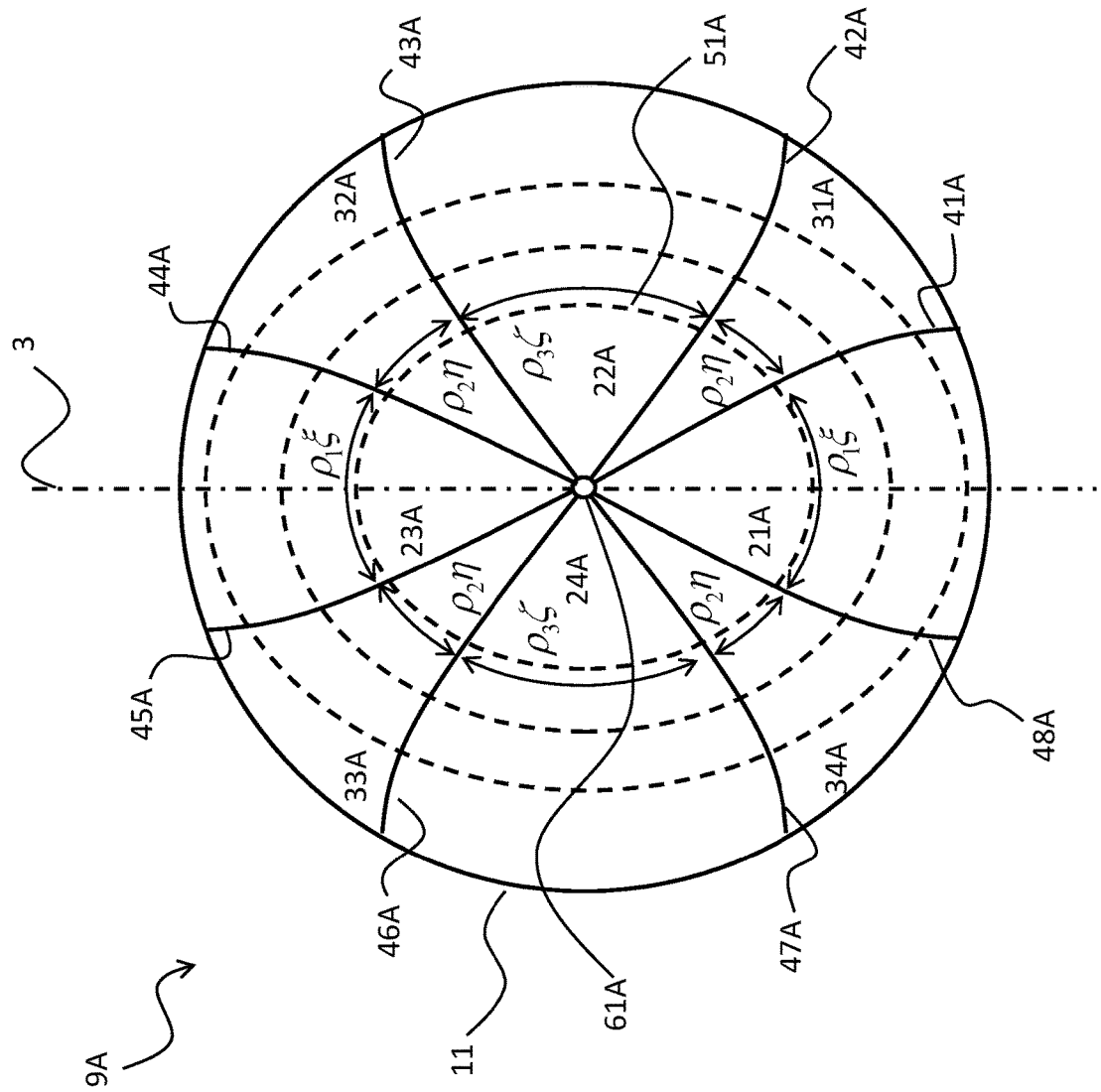
FIG. 9 is a plan view of the magnetic pole surface in a case where the beam track is not decentered in the accelerator magnet device according to the first embodiment.
Figure 10:
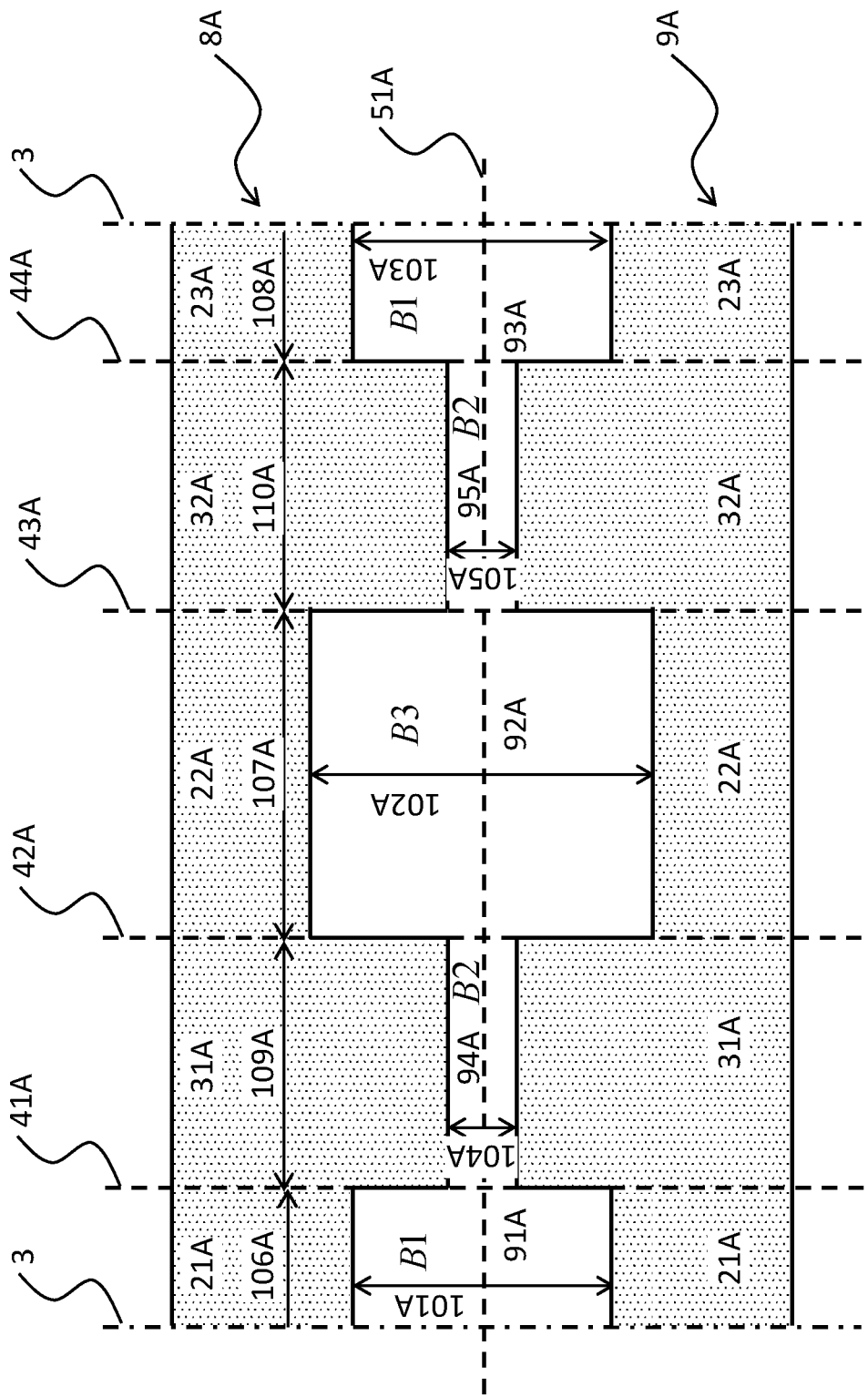
FIG. 10 is a cross-sectional view along the beam track of the magnetic pole illustrated in FIG. 9.

Next, an example of a magnet device in which the type of the valley of the sector type cyclotron has two types will be described with reference to FIG. 9 and FIG. 10. FIG. 9 is a plan view of a lower magnetic pole 9A of a magnet device of another example of the sector type cyclotron of the present embodiment. FIG. 10 is a cross-sectional view of an upper magnetic pole 8A and the lower magnetic pole 9A along a beam track 51A illustrated in FIG. 9.

As illustrated in FIG. 9, in the magnet device of the example, for the concave part, concave parts 21A, 23A, and concave parts 22A, 24A having two different types of shapes and areas are included, and concave parts (a combination of the concave part 21A and the concave part 23A, and a combination of the concave part 22A and the concave part 24A) facing each other across the space 61 have the same shape and area.

Here, a beam curvature radius in the concave parts 21A and 23A is set as $\rho_1$, a beam deflection angle thereof is set as $\xi$, a beam curvature radius in convex parts 31A, 32A, 33A and 34A is set as $\rho_2$, a beam deflection angle thereof is set as $\eta$, a beam curvature radius in the concave parts 22A and 24A is set as $\rho_3$, and a beam deflection angle thereof is set as $\zeta$. In addition, the magnetic field intensity in the concave parts 21A and 23A is set as B1, the magnetic field intensity in the convex parts 31A, 32A, 33A and 34A is set as B2, the magnetic field intensity in the concave parts 22A and 24A is set as B3, and the average magnetic field along the beam track is set as B. Then, relationships illustrated in following Equations (3) and (4) are established.

$$\frac{\xi}{2} + \eta + \frac{\zeta}{2} = \frac{\pi}{2} \quad \text{(Equation 3)}$$

$$\frac{B2-B1}{B1}\xi + \frac{B2-B3}{B}\zeta = \frac{B2-B}{B}\pi \quad \text{(Equation 4)}$$

Based on the Equations (3) and (4), by setting the magnetic field intensity B3 in the concave part 22A and the concave part 24A weaker than the magnetic field intensity B1 of the concave part 21A and the concave part 23A, the beam track as illustrated in FIG. 9 is substantially elliptical in which a major axis is included in the vertical symmetry plane 3, and a minor axis is vertical to the vertical symmetry plane 3.

Here, when the average magnetic field B' of Equation (2) and the average magnetic field B of Equation (4) are the same, if the beam energies are equal, a length of the beam track in FIG. 6 and a length of the beam track in FIG. 9 are equal. However, in FIG. 6, the beam track is substantially circular, while in FIG. 9, the beam track is substantially elliptical.

Therefore, under a condition where the average magnetic fields in FIG. 6 and FIG. 9 are equal, a beam turn separation in the concave part 21A or the concave part 23A illustrated in FIG. 9 is larger than the beam turn separation in the concave part 521 or the concave part 523 illustrated in FIG. 6. On the contrary, the beam turn separation in the concave part 22A or the concave part 24A illustrated in FIG. 9 is smaller than the beam turn separation in the concave part 522 or the concave part 524 illustrated in FIG. 6.

In addition, since the magnetic field intensity B3 in the concave parts 22A and 24A is weaker than the magnetic field intensity B1 in the concave parts 21A and 23A, as illustrated in FIG. 10, a magnetic pole interval 102A is wider than a magnetic pole interval 101A or a magnetic pole interval 103A. In addition, a magnetic pole width 106A of the concave part 21A and a magnetic pole width 108A of the concave part 23A have the same value ($\rho_1\xi$), while a magnetic pole width 107A ($\rho_3\zeta$) of the concave part 22A is wider than magnetic pole widths 106A and 108A ($\rho_1\xi$).

In FIG. 10, magnetic pole intervals 104A and 105A have the same value, and a magnetic pole width 109A of the convex part 31A and a magnetic pole width 110A of the convex part 32A have the same value ($\rho_2\eta$).

In a case where the beam track is decentered, the magnetic pole shape as previously illustrated in FIG. 4 is prepared so as to be the same as in FIG. 9 in a case where the magnetic field is along the beam track. Therefore, the beam track is substantially elliptical. Therefore, it is possible to set the beam turn separation in the concave part 23 larger than the beam turn separation in the concave part 723 illustrated in FIG. 8. Thus, by increasing the beam turn separation, the energy selection efficiency in beam extraction can be further increased, and the extraction efficiency is further improved.

Next, effects of the present embodiment will be described.

The particle beam therapy apparatus 1001 according to the first embodiment of the invention includes the accelerator 1004, and the accelerator 1004 includes the magnet device 1 which includes the disk-shaped upper return yoke 4 and lower return yoke 5, and the pair of upper magnetic pole 8, 8A and lower magnetic pole 9, 9A respectively fixed to the disk-shaped surface of the upper return yoke 4 and the disk-shaped surface of the lower return yoke 5, in which the space to circulate and accelerate the ion beam is formed between the upper magnetic pole 8, 8A and the lower magnetic pole 9, 9A, and the upper magnetic pole 8, 8A and the lower magnetic pole 9, 9A have a plurality of concave parts 21 to 24, 21A to 24A and convex parts 31 to 34, 31A to 34A along the track along which the ion beam circulates, and are plane-symmetrical with respect to the horizontal symmetry plane 2 formed by the track along which the ion beam circulates, and are plane-symmetrical to one of the vertical planes vertical to the horizontal symmetry plane 2, and the magnetic pole intervals 101 to 103, 101A to 103A between the concave parts 21 to 24, 21A to 24A of the upper magnetic pole 8, 8A and the lower magnetic pole 9, 9A are different from each other.

Thus, the curvature of the ion beam track in the region sandwiched between the concave parts 22, 24, 22A and 24A having a large vertical interval can be made smaller than the curvature of the ion beam track in the region sandwiched by the concave parts 21, 23, 21A and 23A having a vertical interval smaller than the concave parts 22, 24, 22A and 24A. Therefore, the ion beam tracks 51 to 53 and 51A can be substantially elliptical, and a beam aggregation region and a beam discrete region in which the turn separation is increased can be formed.

In addition, there are convex parts having different shapes and convex parts having the same shape when the plurality of convex parts 31 to 34 are projected onto the horizontal symmetry plane 2 along which the ion beam circulates, and the magnetic pole interval 102 of the concave parts 22 and 24 sandwiched between the convex part 31 and the convex part 32 or between the convex part 33 and the convex part 34 that have different shapes is larger than the magnetic pole intervals 101 and 103 of the concave parts 21 and 23 sandwiched between the convex part 32 and the convex part 33 or between the convex part 31 and the convex part 34 that have substantially a congruent shape. Since the convex parts having different shapes and the convex parts having the same shape when the plurality of convex structures 31 to 34 are projected onto the horizontal symmetry plane 2 along which the ion beam circulates are provided as described above, it is possible to form an aggregation region where the beam turn separation is dense and a discrete region where the beam turn separation is sparse. Therefore, further narrowing of the beam aggregation region and further enlargement of the discrete region can be achieved, and the beam extraction efficiency can be further improved.

Further, since the beam extraction electromagnets 12 and 13 are further provided in the space of the concave part 23 sandwiched between the convex parts 32, 33 having substantially a congruent shape when projected onto the horizontal symmetry plane 2, the beam turn separation is increased, the beam extraction electromagnets 12 and 13 are disposed in a region having a high energy selection efficiency in beam extraction, so that the beam can be extracted with high accuracy.

Second Embodiment

Figure 11:
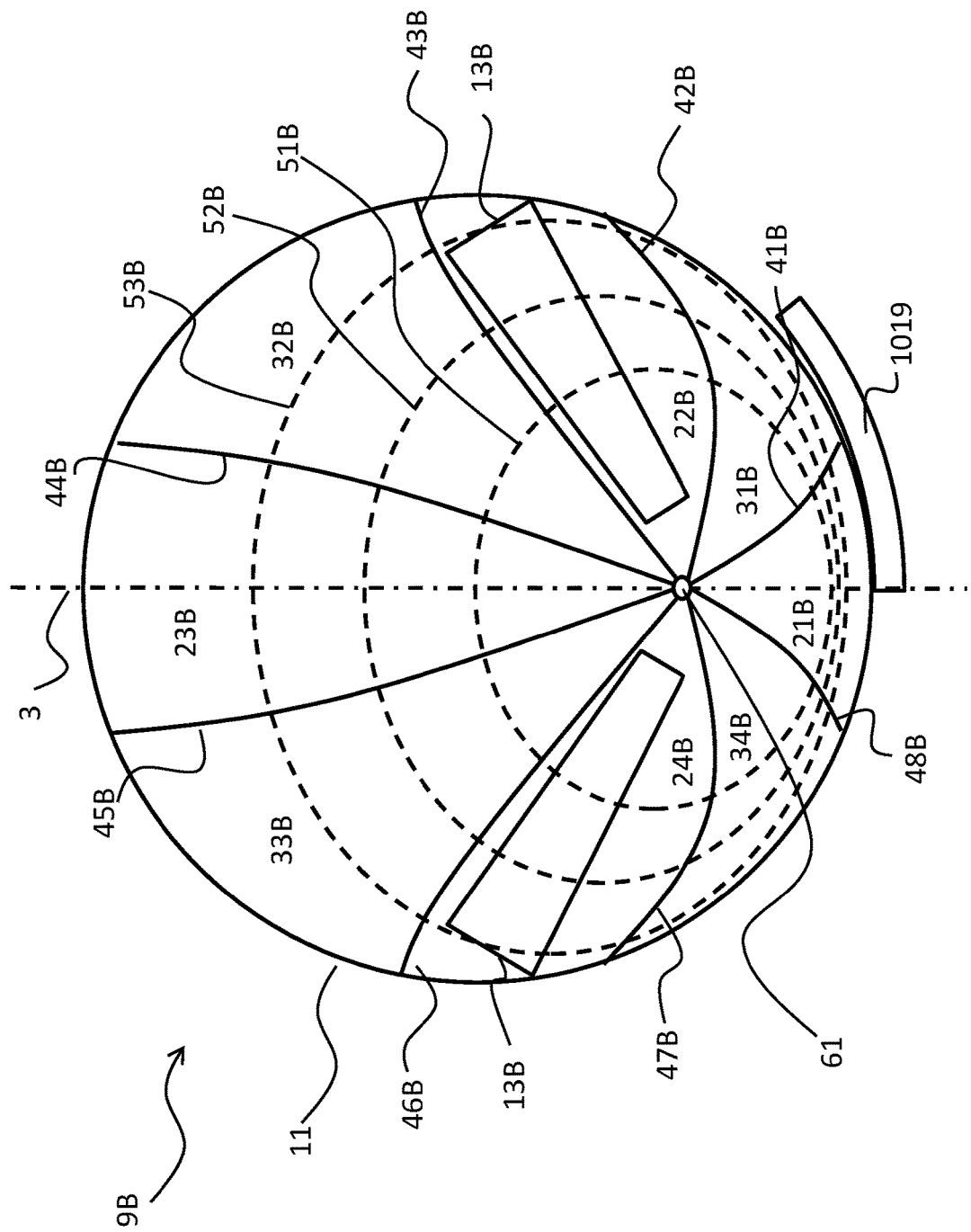
FIG. 11 is a plan view of a magnetic pole surface of a magnet device according to a second embodiment.

A particle beam accelerator and a particle beam therapy apparatus according to a second embodiment of the invention will be described with reference to FIG. 11 and FIG. 12. FIG. 11 is a plan view of a lower magnetic pole 9B of a magnet device according to the second embodiment.

As illustrated in FIG. 4, the extraction electromagnets 12 and 13 are provided at the position of the concave part 23 in the first embodiment, but as illustrated in FIG. 11, extraction electromagnets 13B are provided at two positions of a concave part 22B and a concave part 24B in the second embodiment. Although not shown, an extraction electromagnet corresponding to the extraction electromagnet 12 of the first embodiment is disposed above the extraction electromagnet 13B.

In a case where the extraction electromagnets 13B are provided at two positions of the concave part 22B and the concave part 24B as described above, the beam extraction efficiency can be improved by increasing the beam turn separation at the two positions.

That is, in the first embodiment, the major axis of the substantially elliptical beam track is included in the vertical symmetry plane 3, and the minor axis thereof is vertical to the vertical symmetry plane 3, while in the second embodiment, the minor axis of the substantially elliptical beam track is included in the vertical symmetry plane 3, and the major axis thereof is vertical to the vertical symmetry plane 3. By setting beam tracks 51B, 52B and 53B to such a substantially elliptical shape, the beam turn separation of the concave part 22B and the concave part 24B provided with the extraction electromagnets 13B is increased, and the beam extraction efficiency can be further improved as compared with the case of the substantially circular beam track as illustrated in FIG. 9 and FIG. 10.

Thus, the following structure is adopted in the magnet device of the particle beam accelerator of the second embodiment. The structure will be described with reference to FIG. 12. FIG. 12 is a cross-sectional view of an upper magnetic pole 8B and a lower magnetic pole 9B along the beam track 51B illustrated in FIG. 11.

As illustrated in FIG. 11, on a magnetic pole surface of the lower magnetic pole 9B, concave parts 21B, 22B, 23B and 24B and convex parts 31B, 32B, 33B and 34B, that are indicated by solid lines in the circulating direction of the beam tracks 51B, 52B and 53B along which the ion beam circulates, are alternately disposed, and are plane-symmetrical with respect to the vertical symmetry plane 3. The extraction electromagnets 13B are disposed directly above the concave part 22B and directly above the concave part 24B.

The concave parts 21B, 22B, 23B, and 24B and the convex parts 31B, 32B, 33B, and 34B are substantially fan-shaped.

As illustrated in FIG. 11, the shapes of the concave parts 21B, 22B, 23B and 24B are not all the same; although the concave part 22B and the concave part 24B are symmetrical with respect to the vertical symmetry plane 3 and have the same area, the concave part 22B and the concave part 24B have shapes and areas different from those of the concave part 21B and the concave part 23B.

As illustrated in FIG. 12, a valley region 91B sandwiched by upper and lower concave parts 21B, a hill region 94B sandwiched between upper and lower convex parts 31B, a valley region 92B sandwiched between upper and lower concave parts 22B, a hill region 95B sandwiched between upper and lower convex parts 32B, and a valley region 93B sandwiched between upper and lower concave parts 23B are arranged along the beam track 51B. Boundary surfaces 41B, 42B, 43B, and 44B, and boundary surfaces 45B, 46B, 47B, and 48B illustrated in FIG. 11 are substantially vertical to the horizontal symmetry plane 2.

Design values of a magnetic pole interval 101B between the upper magnetic pole 8B and the lower magnetic pole 9B in the valley region 91B, a magnetic pole interval 102B between the upper magnetic pole 8B and the lower magnetic pole 9B in the valley region 92B, and a magnetic pole interval 103B between the upper magnetic pole 8B and the lower magnetic pole 9B in the valley region 93B are not the same value, but different values, and the magnetic pole interval 102B is smaller than the magnetic pole interval 101B and the magnetic pole interval 103B. Therefore, a magnetic field B3″ in the valley region 92B is stronger than a magnetic field B1″ in the valley region 91B and the valley region 93B. A substantially elliptical beam track in which the major axis is vertical to the vertical symmetry plane 3 can be realized by adjusting the magnetic pole interval and the magnetic field intensity as described above.

Similarly, design values of a magnetic pole interval 104B in the hill region 94B and a magnetic pole interval 105B in the hill region 95B are also different.

In addition, in the magnet device of the present embodiment, a magnetic pole width 106B of the concave part 21B, a magnetic pole width 107B of the concave part 22B, and a magnetic pole width 108B of the concave part 23B are not the same width, but different widths. Further, a magnetic pole width 109B of the convex part 31B and a magnetic pole width 110B of the convex part 32B are also different.

Other components and operations are substantially the same as those of the particle beam accelerator and the particle beam therapy apparatus 1001 including the same according to the first embodiment, and detailed description thereof is omitted.

The particle beam accelerator and the particle beam therapy apparatus according to the second embodiment of the invention have substantially the same effects as those of the particle beam accelerator and the particle beam therapy apparatus of the first embodiment.

In addition, there are convex parts having different shapes and convex parts having the same shape when the plurality of convex parts 31B to 34B are projected onto the horizontal symmetry plane 2 along which the ion beam circulates, and the magnetic pole interval 102B of the concave parts 22B and 24B sandwiched between the convex part 31B and the convex part 32B or between the convex part 33B and the convex part 34B that have different shapes is smaller than the magnetic pole intervals 101B and 103B of the concave parts 21B and 23B sandwiched between the convex parts 32B and the convex part 33B, or between the convex parts 31B and the convex part 34B that have substantially a congruent shape, so that it is possible to form an aggregation region where the beam turn separation is dense and a discrete region where the beam turn separation is sparse, and thus the beam extraction efficiency can be further improved.

Further, the magnetic field intensity B3″ between the concave parts 22B and 24B sandwiched between the convex part 31B and the convex part 32B or between the convex part 33B and the convex part 34B that have different shapes when projected onto the horizontal symmetry plane 2 is stronger than the magnetic field intensity B1″ between the concave parts 21B and 23B sandwiched between the convex part 32B and the convex part 33B or between the convex part 31B and the convex part 34B that have substantially a congruent shape, so that it is possible to form an aggregation region where the beam turn separation is dense and a discrete region where the beam turn separation is sparse, and thus the beam extraction efficiency can be further improved.

Further, since the beam extraction electromagnet 13B is further provided in the space of the concave parts 22B and 24B sandwiched between the convex part 31B and the convex part 32B or between the convex part 33B and the convex part 34B, the beam turn separation is increased, and since the beam extraction electromagnet 13B is disposed at a region having a high energy selection efficiency in beam extraction, the beam can be extracted with high accuracy.

Other Modifications

The invention is not limited to the above embodiments, and includes various modifications. The embodiments described above have been described in detail for easy understanding of the invention, and the invention is not necessarily limited to those including all the configurations described above.

REFERENCE SIGN LIST 1 magnet device
2 horizontal symmetry plane (track plane)
3 vertical symmetry plane (vertical plane)
4 upper return yoke
5 lower return yoke
6 coil
7 vacuum container
8, 8A, 8B upper magnetic pole
9, 9A, 9B lower magnetic pole
10 magnetic pole surface
12, 13, 13B extraction electromagnet
21, 21A, 21B, 22, 22A, 22B, 23, 23A, 23B, 24, 24A, 24B concave part
31, 31A, 31B, 32, 32A, 32B, 33, 33A, 33B, 34, 34A, 34B convex part
41, 41A, 41B, 42, 42A, 42B, 43, 43A, 43B, 44, 44A, 44B, 45, 45A, 45B, 46, 46A, 46B, 47, 47A, 47B, 48, 48A, 48B boundary surface
51, 51A, 51B, 52, 52B, 53, 53B beam track
61 space (incident position)
91, 91A, 91B, 92, 92A, 92B, 93, 93A, 93B valley region
94, 94A, 94B, 95, 95A, 95B hill region
101, 101A, 101B, 102, 102A, 102B, 103, 103A, 103B, 104, 104A, 104B, 105, 105A, 105B magnetic pole interval
106, 106A, 106B, 107, 107A, 107B, 108, 108A, 108B, 109, 109A, 109B, 110, 110A, 110B magnetic pole width
1001 particle beam therapy apparatus

The invention claimed is:
1. A particle beam accelerator, comprising:
a magnet device that includes return yokes, and a pair of magnetic poles fixed to flat surfaces of the return yokes, wherein
a space to circulate and accelerate an ion beam is formed between the pair of magnetic poles, and the pair of magnetic poles have a plurality of concave structures and convex structures along a track along which the ion beam circulates, are plane-symmetrical with respect to a track plane formed by the track along which the ion beam circulates, and are plane-symmetrical to one of vertical planes vertical to the track plane, and
distances between the plurality of concave structure parts of the pair of magnetic poles are different.
2. The particle beam accelerator according to claim 1, wherein there are convex parts having different shapes and convex parts having substantially a congruent shape when the plurality of convex structures are projected onto the track plane along which the ion beam circulates, and an interval of concave parts sandwiched between the convex parts having different shapes is larger than an interval of concave parts sandwiched between the convex parts having substantially a congruent shape.

3. The particle beam accelerator according to claim 2, further comprising:

a beam extraction electromagnet that is provided in a space of the concave part sandwiched between the convex parts having substantially a congruent shape.

4. The particle beam accelerator according to claim 1, wherein there are convex parts having different shapes and convex parts having substantially a congruent shape when the plurality of convex structures are projected onto the track plane along which the ion beam circulates, and an interval of concave parts sandwiched between the convex parts having different shapes is smaller than an interval of concave parts sandwiched between the convex parts having substantially a congruent shape.

5. The particle beam accelerator according to claim 4, wherein a magnetic field intensity between the concave parts sandwiched between the convex parts having different shapes is stronger than an magnetic field intensity between the concave parts sandwiched between the convex parts having a substantially congruent shape.

6. The particle beam accelerator according to claim 5, further comprising:

a beam extraction electromagnet that is provided in a space of the concave part sandwiched between the convex parts having different shapes.

7. A particle beam therapy apparatus, comprising:

the particle beam accelerator according to claim 1.

* * * * *